United States Patent [19]

Hrebeniuk

[11] Patent Number: Plant 6,325

[45] Date of Patent: Oct. 4, 1988

[54] POINSETTIA PLANT NAMED HL-1 PINK AND WHITE

[76] Inventor: Alexander Hrebeniuk, Rd. #1, Box 118, Sugar Run, Pa. 18846

[21] Appl. No.: 892,073

[22] Filed: Aug. 1, 1986

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Schwartz, Jeffery, Schwaab, Mack, Blumenthal & Evans

[57] ABSTRACT

A poinsettia plant named HL-1 Pink and White particularly characterized by its bicolor pink and white bracts, early and long blooming period, superior self-branching, fast rooting habit, ability to be grown in relatively cool temperatures, excellent retention of foliage and bract color, its double flowers, and by its compact growth.

2 Drawing Sheets

The present invention relates to a new and distinct cultivar of poinsettia plant known by the cultivar name HL-1 Pink and White, and botanically known as *Euphorbia pulcherrima.*

HL-1 Pink and White was discovered as a natural sport found growing by applicant in a bed of plants of the parent cultivar HL-1 Red in Sugar Run, Pa. in November of 1984. HL-1 Red is disclosed in applicant's U.S. Plant Pat. No. 4,434, dated July 10, 1979, with the parent cultivar being introduced commercially under the cultivar designation Noel.

The first act of asexual reproduction of HL-1 Pink and White was accomplished when vegetative cuttings were taken from the initial selection in May of 1985 in a controlled environment in Sugar Run, Pa. by applicant. Horticultural examination of selected units initiated in November of 1985 has demonstrated that the combination of characteristics as herein disclosed for HL-1 Pink and White are firmly fixed and are retained through successive generations of asexual reproduction.

HL-1 Pink and White has not been observed under all possible environmental conditions. The phenotype may vary significantly with variations in environment such as temperature, light intensity, and day length. The following observations, measurements and comparisons describe plants grown in Sugar Run, Pa. under greenhouse conditions which approximate those generally used in commercial practice.

The following traits have been repeatedly observed and are determined to be basic characteristics of HL-1 Pink and White which in combination distinguish this poinsettia as a new and distinct cultivar:

1. It has the ability to produce 10 branches from a single pinched plant without chemical treatment.
2. Can start blooming before Christmas and as early as the second week in November, and stays in bloom for three months, without loss of foliage or flowers.
3. Can be initially grown at 65 degrees F., which can be lowered to 58–60 degrees F. when half bloomed.
4. Has double flowers which are resistant to fade.
5. Can be watered without "dark spotting" resulting.
6. Has hardy foliage which is resistant to drooping.
7. Self-branching, with many branches being produced.
8. Fast rooting cuttings.
9. Pointed leaves.
10. Resists bruising which makes it good for shipping.

11. Compact plant, with decreased tendency of the butts to separate.
12. The foliage and flowers retain their color for a longer period of time without fading, whether or not the plant is exposed to sun.
13. Greater resistance to root rot.

The accompanying photographic drawings show typical inflorescence and foliage characteristics of HL-1 Pink and White with colors being as nearly true as possible with illustrations of this type. Sheet 1 is a front perspective view of the cultivar. Sheet 2 is a comparison view of the bracts of HL-1 Pink and White, which appears on the left, and V-10 Marble, a commercial cultivar, which appears on the right. The developing bract shape will be apparent, as will the full leaf shape of the respective cultivars appearing at the very bottom. The developing bract shapes have been colored in to depict true color.

Although the new cultivar is unique in many respects, it can be compared with in terms of its variegated bract characteristics with the cultivar V-10 Marble. The latter has a deep red-grey color near the midrib, with the background color being a dark cream. In the new cultivar, the color near the midrib is a pale pink, and the background color essentially white.

In the following description color references are made to The Royal Horticultural Society Colour Chart. The color values were determined at approximately 4:50 p.m. on July 8, 1986 under fluorescent light at Parrish, Fla.

Classification:

*Botanical.*—*Euphorbia pulcherrima.*

*Commercial.*—Poinsettia.

Parentage: Sport of HL-1 Red.

Plant description:

(A) *Form.*—Double.

(B) *Growth habit.*—Upright, medium height and self-branching.

(C) *Rooting.*—Very fast, roots develop within two weeks and are rot resistant.

(D) *Blooming season.*—Nine week variety, starting mostly in the second week of November.

(E) *Blooming habit.*—Large bracts in double rows.

Foliage:

(A) *Size.*—Up to 20 cm long and 9 cm wide.

(B) *Quantity.*—10 to 20 leaves or more.

(C) *Color.*—New foliage: Upper side, 147B; under side, 147C. Old foliage: Upper side, 147A; under side 147B.

(D) *Shape.*—Generally ovate, venation midrib to margin, tips apiculate.

(E) *Texture.*—Upper side, flat; under side, smooth.

(F) *Edge of margin.*—Repand.

(G) *Disease resistance.*—Some resistance observed to root rot.

Flowers:

(A) *Borne.*—Compound Corymb.

(B) *Quantity.*—Excellent.

(C) *Continuity.*—Flowers continuously for up to three months.

Bracts:

(A) *Size.*—Up to 20 cm long and 9 cm wide.

(B) *Quantity.*—From 18–20 per stem.

(C) *Shape.*—Ovate with a repand margin.

(D) *Color.*—51D in center of leaf along the midrib, spreading out unevenly toward the margin. The outer portion is 155A creamy white. There may be some lightening of the pink color as the bract matures, as shown in sheet 2.

Reproductive organs: Typical poinsettia.

I claim:

1. A new and distinct cultivar of poinsettia plant, named HL-1 Pink and White, as described and illustrated, and particularly characterized by its variegated pink and white bracts, early and long blooming period, superior self-branching, fast rooting habit, ability to be grown in relatively cool temperatures, excellent retention of foliage and bract color, its double flowers, and its compact growth.

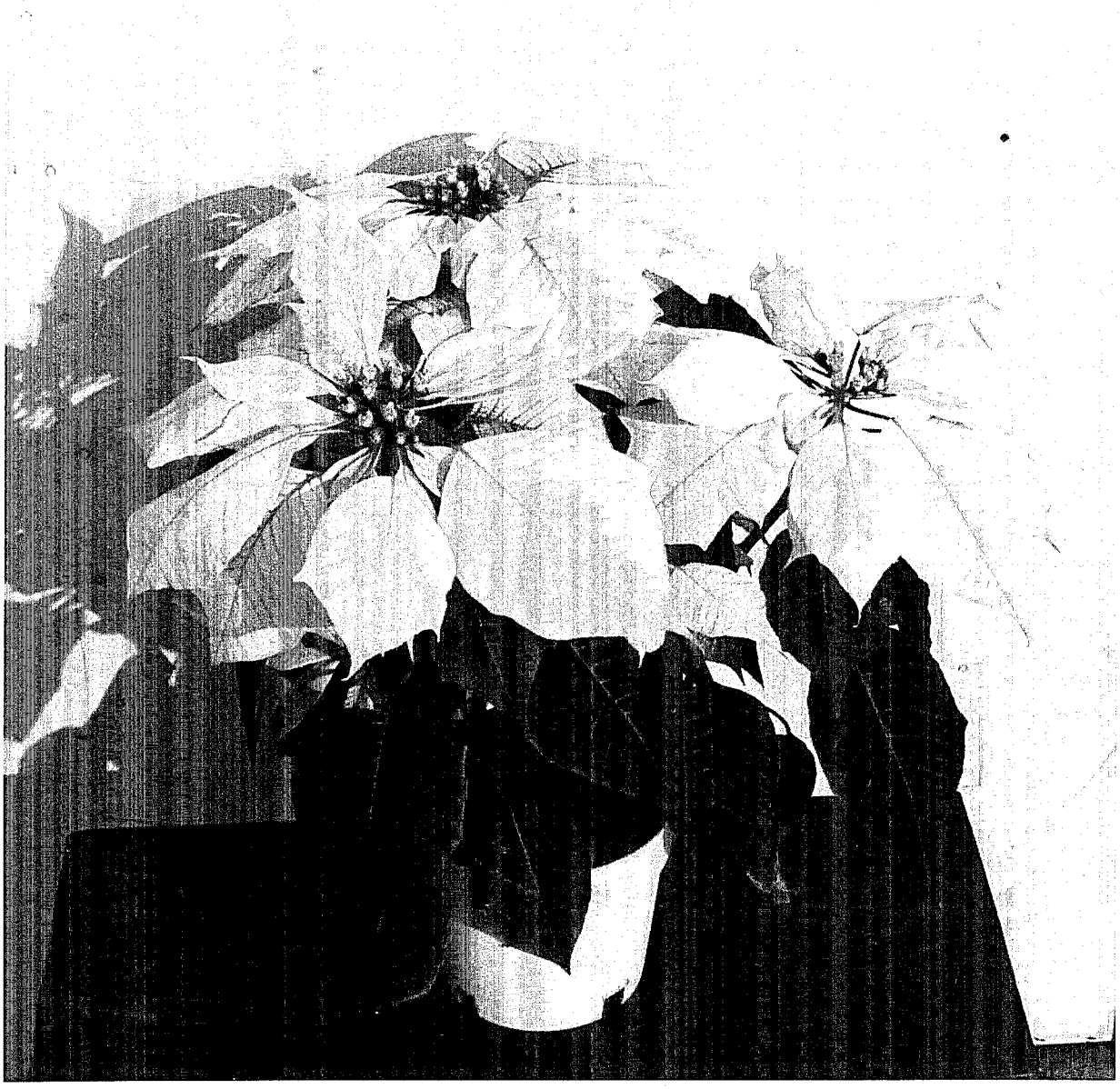

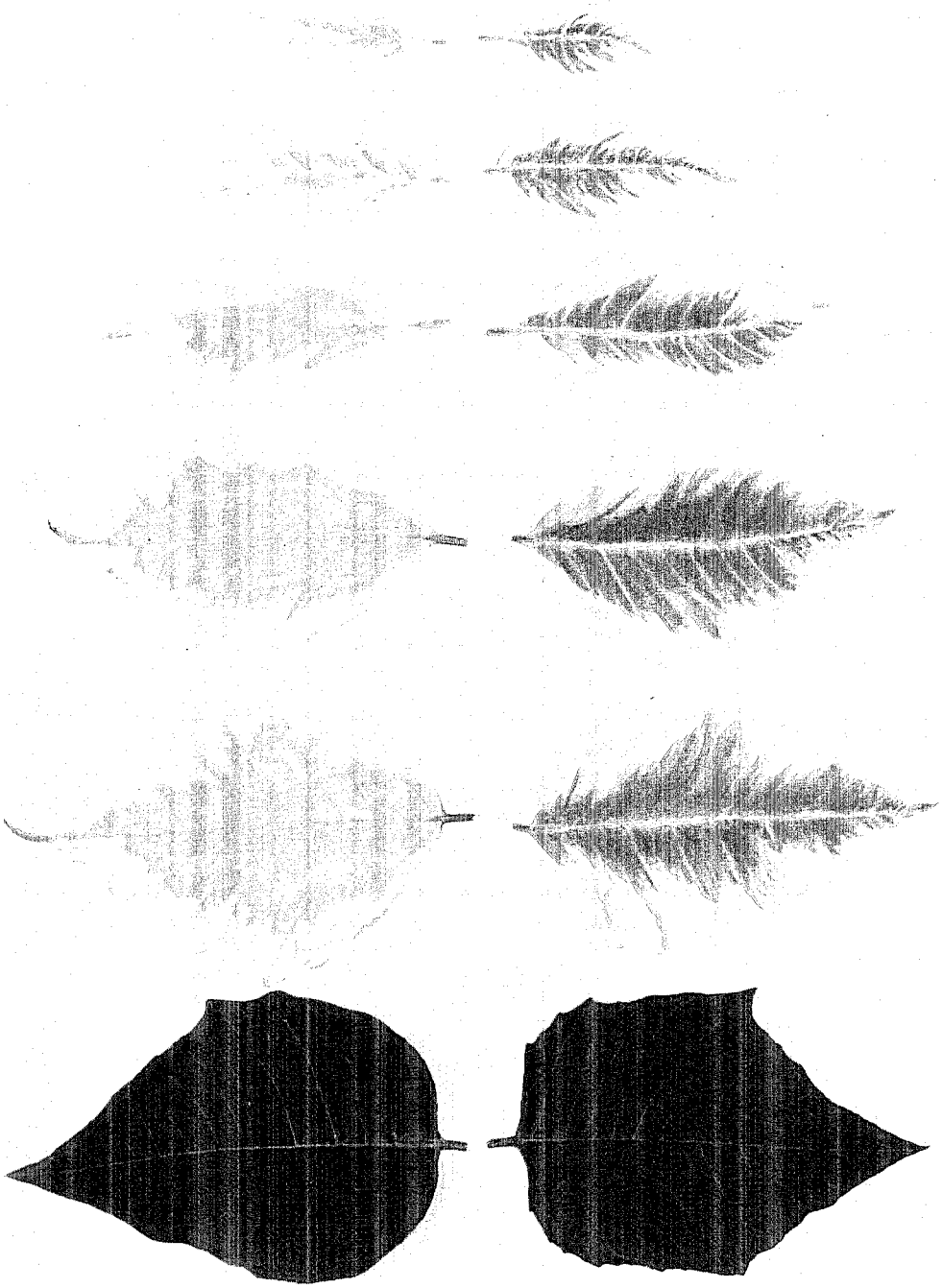

* * * * *